United States Patent
Parquet et al.

(10) Patent No.: US 7,967,858 B2
(45) Date of Patent: Jun. 28, 2011

(54) DEVICE FOR RAPID CONNECTION BETWEEN A TOTALLY IMPLANTABLE HEART PROSTHESIS AND NATURAL AURICLES

(75) Inventors: Jean-Marc Parquet, Domont (FR); Alain Carpentier, Paris (FR)

(73) Assignee: Carmat, Paris (FR)

(*) Notice: Subject to any disclaimer, the term of this patent is extended or adjusted under 35 U.S.C. 154(b) by 216 days.

(21) Appl. No.: 12/304,454

(22) PCT Filed: Jun. 11, 2007

(86) PCT No.: PCT/FR2007/000959
§ 371 (c)(1),
(2), (4) Date: Dec. 11, 2008

(87) PCT Pub. No.: WO2007/144495
PCT Pub. Date: Dec. 21, 2007

(65) Prior Publication Data
US 2009/0204206 A1    Aug. 13, 2009

(30) Foreign Application Priority Data
Jun. 15, 2006   (FR) ..................................... 06 05331

(51) Int. Cl.
*A61M 1/12*   (2006.01)
(52) U.S. Cl. ........................................ 623/3.26; 623/3.1
(58) Field of Classification Search .................. 623/3.26, 623/2.4, 2.41, 3.1–3.3
See application file for complete search history.

(56) References Cited

U.S. PATENT DOCUMENTS

| 4,994,078 | A | * | 2/1991 | Jarvik | 623/3.14 |
| 5,089,014 | A |  | 2/1992 | Holfert |  |
| 5,109,878 | A | * | 5/1992 | Kuo-Hua | 132/279 |
| 5,135,539 | A |  | 8/1992 | Carpentier |  |
| 5,776,186 | A | * | 7/1998 | Uflacker | 606/194 |
| 6,030,392 | A | * | 2/2000 | Dakov | 606/139 |

FOREIGN PATENT DOCUMENTS
EP    0 324 669    7/1989

OTHER PUBLICATIONS
International Search Report dated Oct. 17, 2007 w/ English translation.
Written Opinion of the International Searching Authority with English translation.
* cited by examiner Primary Examiner — David Isabella
Assistant Examiner — Suba Ganesan
(74) Attorney, Agent, or Firm — Dickinson Wright PLLC

(57) ABSTRACT

Device for rapid connection between a totally implantable heart prosthesis and natural articles. According to the invention, said prosthesis comprises: fastening means (16, 25) for fastening an end of one of the lunettes (2, 3) to the other lunette (3, 2), said fastening means being able to permit folding of said lunettes relative to each other; guide means (10, 11, 20, 21) for guiding said lunettes relative to each other before and during fastening and also during folding; and snap-fit means (19, 26) for engaging said lunettes on each other in the operating position corresponding to the end of said folding.

9 Claims, 4 Drawing Sheets

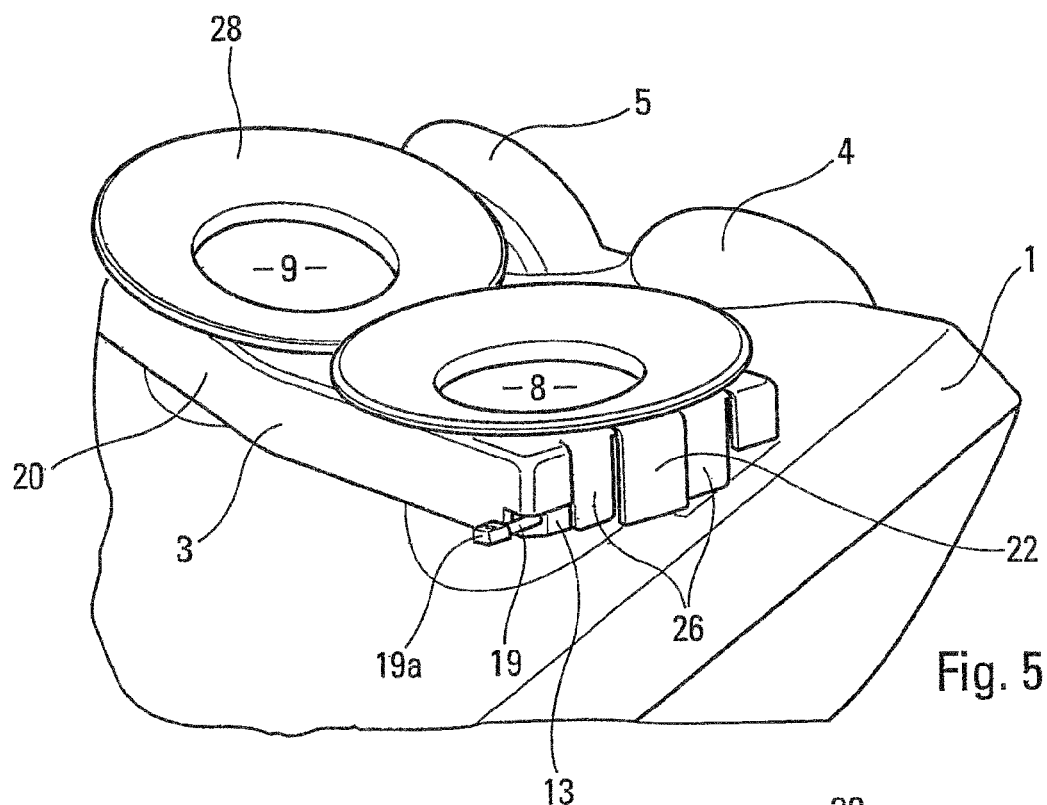
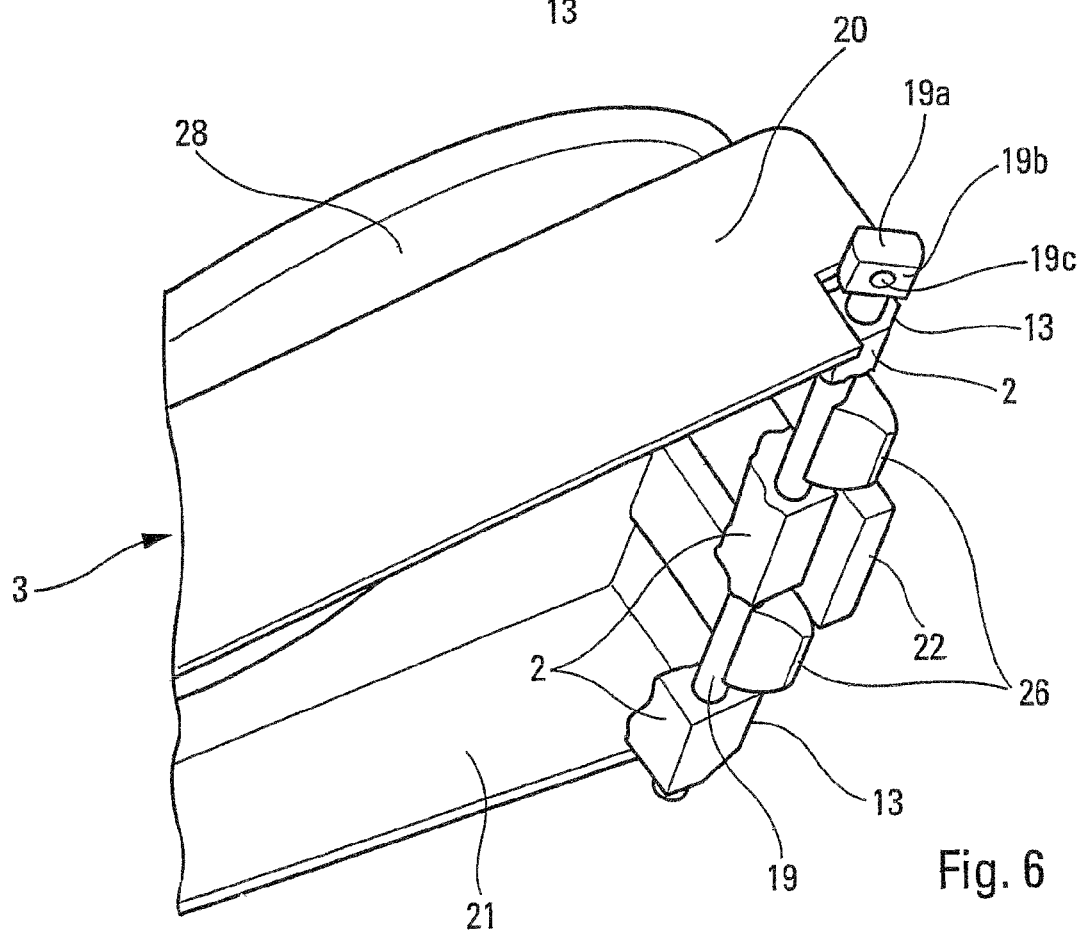

DEVICE FOR RAPID CONNECTION BETWEEN A TOTALLY IMPLANTABLE HEART PROSTHESIS AND NATURAL AURICLES

The present invention relates to a device for rapid connection between a totally implantable heart prosthesis and natural auricles.

Document U.S. Pat. No. 5,135,539 has already disclosed a heart prosthesis of this type implantable in the pericardial cavity of a patient and able to replace the natural left and right ventricles of said patient after their removal. This heart prosthesis comprises a rigid body in which artificial left and right ventricles are arranged, said artificial ventricles being provided with means for rapid connection to the natural left and right auricles of said patient, comprising:

- a first bezel forming an integral part of said rigid body and comprising first and second orifices which communicate respectively with the artificial left ventricle and with the artificial right ventricle by way of valves; and
- a second bezel comprising third and fourth orifices that can be connected respectively to said natural left auricle and to said natural right auricle.

In this embodiment, said first and second bezels can be connected to each other removably, in order to assume an operative position in which said first and third orifices are located opposite each other and said second and fourth orifices are located opposite each other.

Such a system of bezels greatly facilitates the connection of said prosthesis to said second bezel, previously connected to said natural auricles. However, on account of the position of the heart prosthesis in the pericardial cavity at the time of implantation, this connection is performed blind, and there is no guarantee that the connection position obtained will be precise and correspond exactly to said operative position.

The object of the present invention is to improve the heart prosthesis described in document U.S. Pat. No. 5,135,539 in order to overcome this disadvantage.

To this end, according to the invention, the heart prosthesis implantable in the pericardial cavity of a patient, said prosthesis being able to replace the natural left and right ventricles of said patient after their removal, and comprising a rigid body in which artificial left and right ventricles are arranged, said artificial ventricles being provided with means for rapid connection to the natural left and right auricles of said patient, comprising:

- a first bezel forming an integral part of said rigid body and comprising first and second orifices which communicate respectively with the artificial left ventricle and with the artificial right ventricle; and
- a second bezel comprising third and fourth orifices that can be connected respectively to said natural left auricle and to said natural right auricle, said first and second bezels being able to be connected to each other removably, in order to assume an operating position in which said first and third orifices are located opposite each other and said second and fourth orifices are located opposite each other, is distinguished by the fact that it comprises:

- fastening means for fastening one end of one of the bezels to the other bezel, said fastening means being able to permit folding of said bezels relative to each other;
- guide means for guiding said bezels relative to each other before and during fastening and also during folding; and
- snap-fit means for engaging said bezels on each other in the operative position corresponding to the end of said folding.

Thus, according to the invention, by means of the cooperation of said fastening means, said guide means and said snap-fit means, not only is the connection of said prosthesis to said second bezel simplified when working blind, but also the snap-fitting can be achieved only if the relative position of said bezels corresponds precisely to said operative position.

Preferably, said snap-fit means are situated, relative to said bezels, remote from said fastening means. Said snap-fit means can comprise elastic hooks carried by one of said bezels, and anchoring means, for anchoring said elastic hooks, carried by the other of said bezels, said anchoring means being removable from the bezel that carries them. Thus, by removing said anchoring means, it is possible to disconnect said second bezel from the prosthesis, if this proves necessary.

Advantageously, said anchoring means are formed by a transverse pin that can slide in said bezel that carries it.

To ensure stable fastening of said second bezel on the first one, it is advantageous that said fastening means comprise a transverse shaft carried by one of said bezels, and a transverse groove which is formed in the other of said bezels and in which said transverse shaft can lodge itself.

Said guide means can comprise at least one longitudinal face on said first bezel and at least one longitudinal face on said second bezel, said longitudinal faces of said first and second bezels coming into contact with one another before fastening, and sliding on one another during said fastening and said folding.

In a preferred embodiment of the present invention, said first and second bezels each have the general shape of a right-angled parallelepiped, said second bezel being able to serve as a cover laterally fitted on said first bezel. Thus, in this case, the two longitudinal faces of said second bezel can cooperate with the two longitudinal faces of said first bezel in order to serve as guide means.

At one of its ends, said transverse pin constituting the anchoring means can be provided with a grip head that has means, for example flats, allowing said pin to be taken hold of securely, without any possibility of rotation, by surgical forceps. Moreover, means can be provided for attaching said pin to the bezel carrying it during the maneuvers for connection of said bezels.

The figures in the attached drawing will show clearly how the invention can be realized. In these figures, identical reference signs designate similar elements.

FIG. 5 is a perspective plan view corresponding to FIG. 2D, the snap-fit pin not being completely engaged, for purposes of clarity of the drawing.

FIG. 6 is a partial and perspective view from the bottom, illustrating the removable snap-fitting of said bezels.

Figure 1:
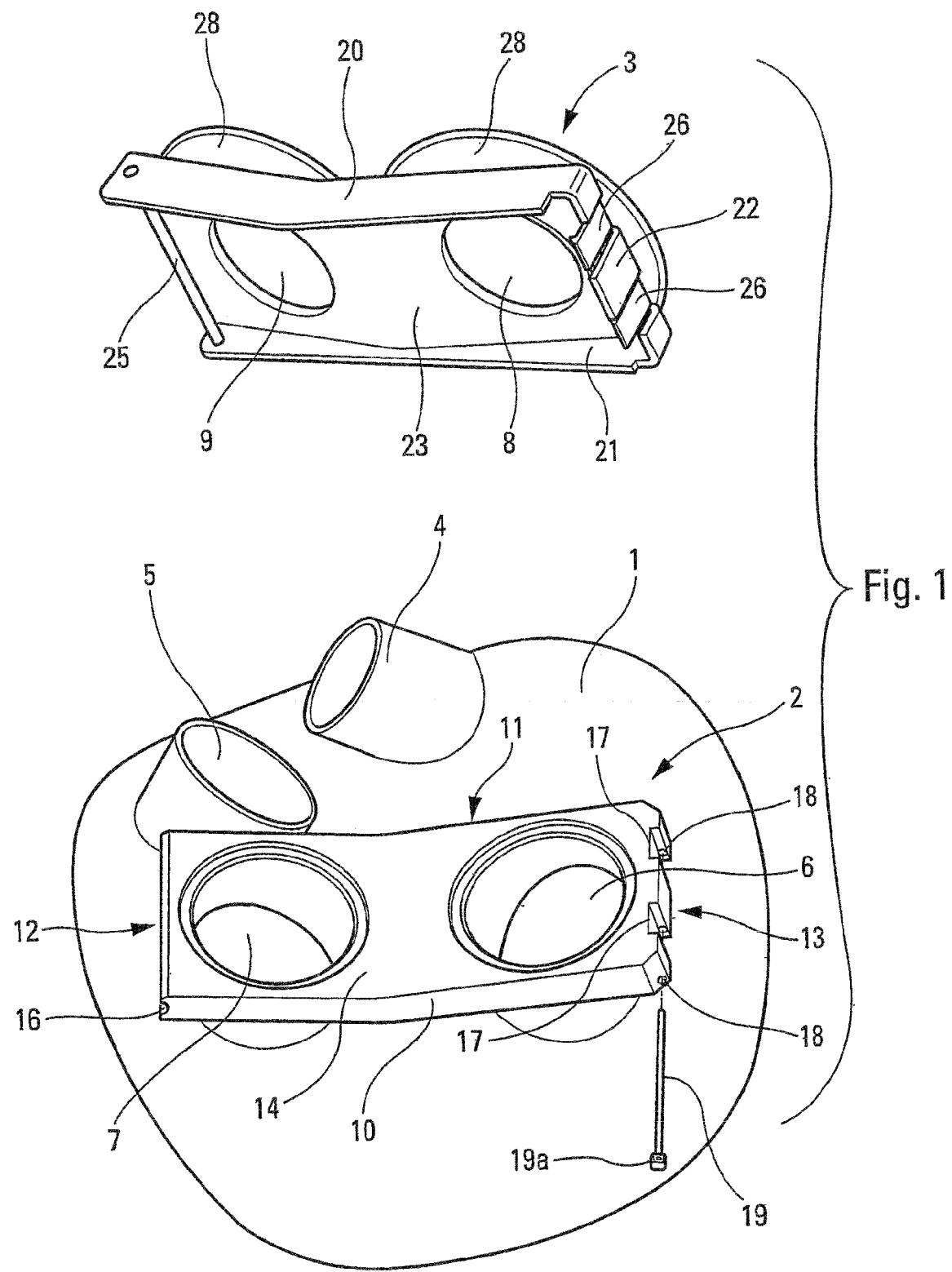
FIG. 1 is an exploded and schematic perspective view of a heart prosthesis according to the present invention.
Figure 2A:
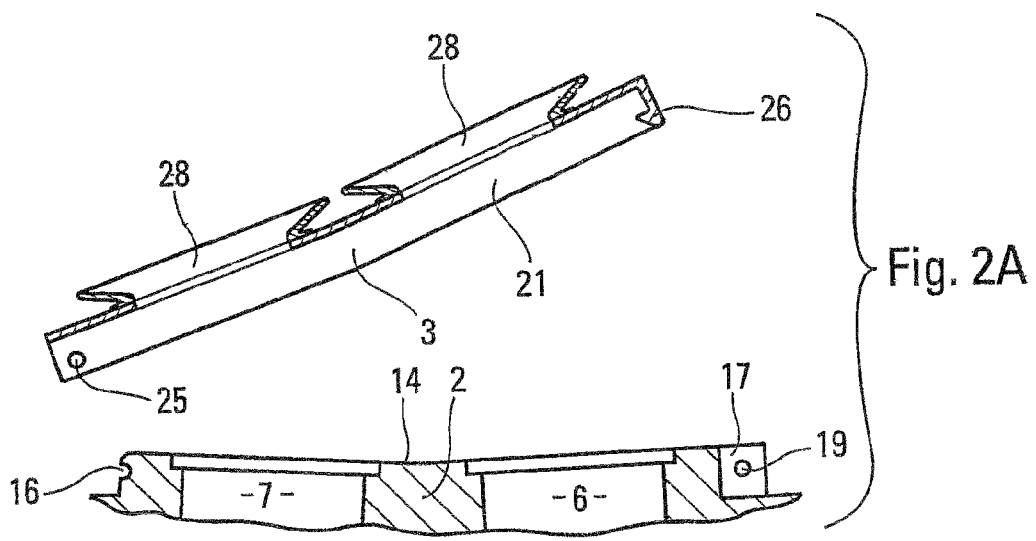
FIGS. 2A, 2B, 2C and 2D illustrate schematically, in longitudinal section, three steps in the assembling of said bezels.
Figure 2B:
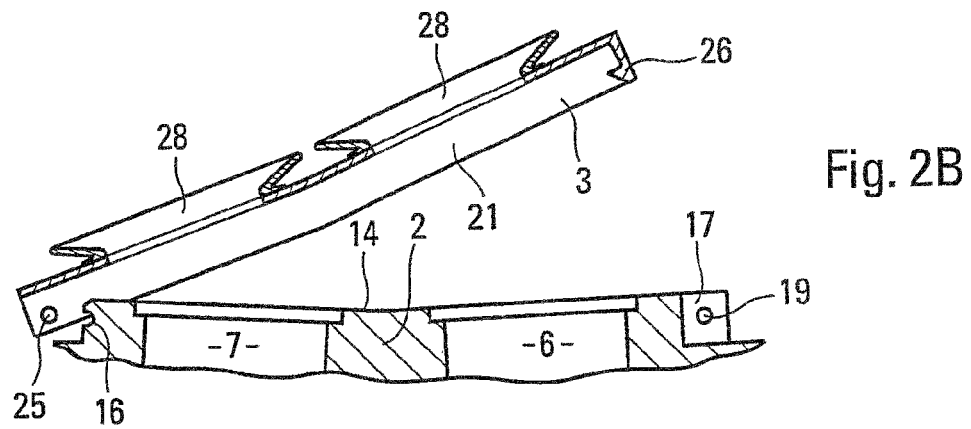
Figure 2C:
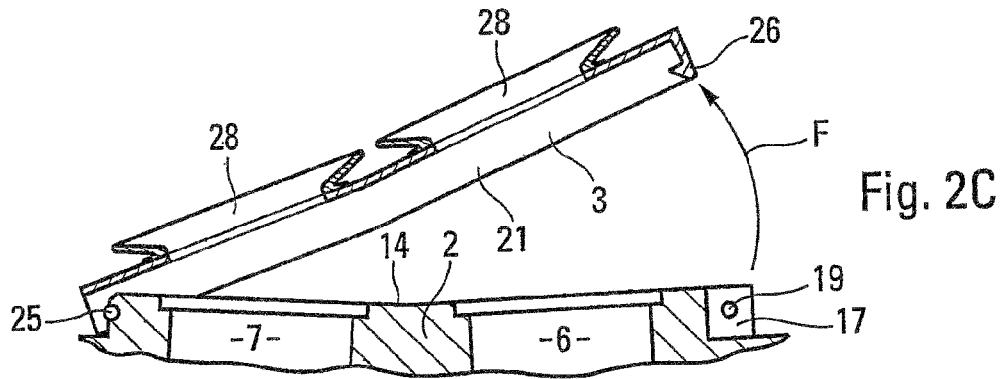
Figure 2D:
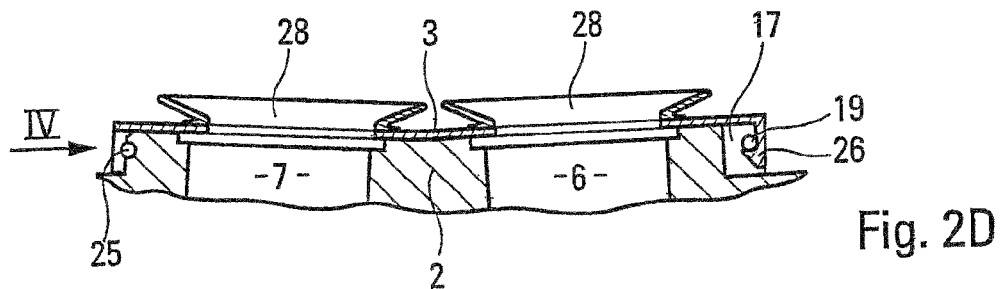

The heart prosthesis according to the present invention, shown in FIG. 1 in an exploded view, is able to replace the natural left and right ventricles of a patient after their removal. It comprises a rigid body 1 in which artificial left and right ventricles (not visible in FIG. 1) are arranged, said ventricles being provided with means 2, 3 for connection to the natural left and right auricles (not visible) of said patient, and means 4, 5, respectively, for connection to the aorta and the pulmonary artery.

The means for connection to said natural left and right auricles comprise:
- a bezel 2 forming an integral part of said rigid body 1 and comprising an orifice 6 which communicates with the artificial right ventricle and an orifice 7 which communicates with the artificial left ventricle, valves (not shown in FIG. 1) being arranged in said orifices 6, 7; and
- a bezel 3 to which the bezel 2 can be connected removably and which comprises orifices 8, 9 that can be arranged opposite said orifices 6 and 7, respectively, when said bezels 2 and 3 occupy the precise relative position corresponding to the functioning of the prosthesis.

The bezel 2 has the general shape of a right-angled parallelepiped provided with two parallel longitudinal side faces 10 and 11, a rear face 12, a front face 13 and an upper face 14.

Figure 3:
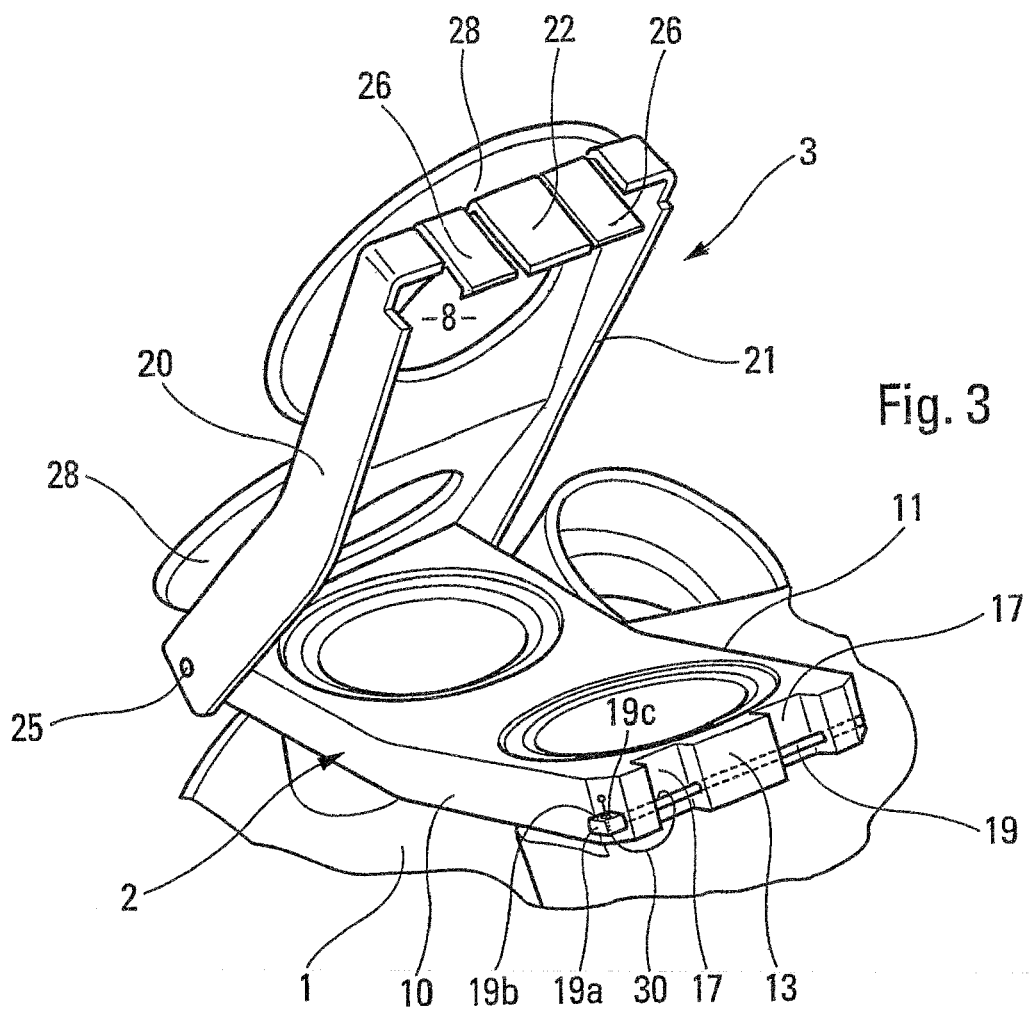
FIG. 3 is a perspective view of the heart prosthesis according to the invention in a position corresponding to FIG. 2C.

The rear face 12 comprises a groove 16' extending transversely with respect to said bezel 2, while the front face 13 comprises notches 17. Moreover, in the area of said front face 13, the bezel 2 has a transverse conduit 18 that passes through said notches 17 and is able to receive a removable pin 19. Thus, when said pin is placed in the conduit 18, it is arranged transversely with respect to said bezel 2 and is exposed as it passes through said notches 17 (see FIGS. 3 and 6).

The bezel 3 has the general shape of the bezel 2, for which it can serve as a cover. Said bezel 3 is provided with two parallel longitudinal side faces 20 and 21, a front face 22 and an upper face 23. The rear face of the bezel 3 is open and traversed by a transverse shaft 25, while the front face 22 comprises one or more elastic hooks 26 located respectively in line with the notch or notches 17. Said elastic hook or hooks can be joined to said bezel 3 or, as is shown in the figures, can form integral parts of the latter, when it is made of an elastic, for example synthetic material.

FIG. 1 also shows, on the bezel 3, individual suture flanges 28 with which the orifices 8 and 9 are provided.

Figure 4:
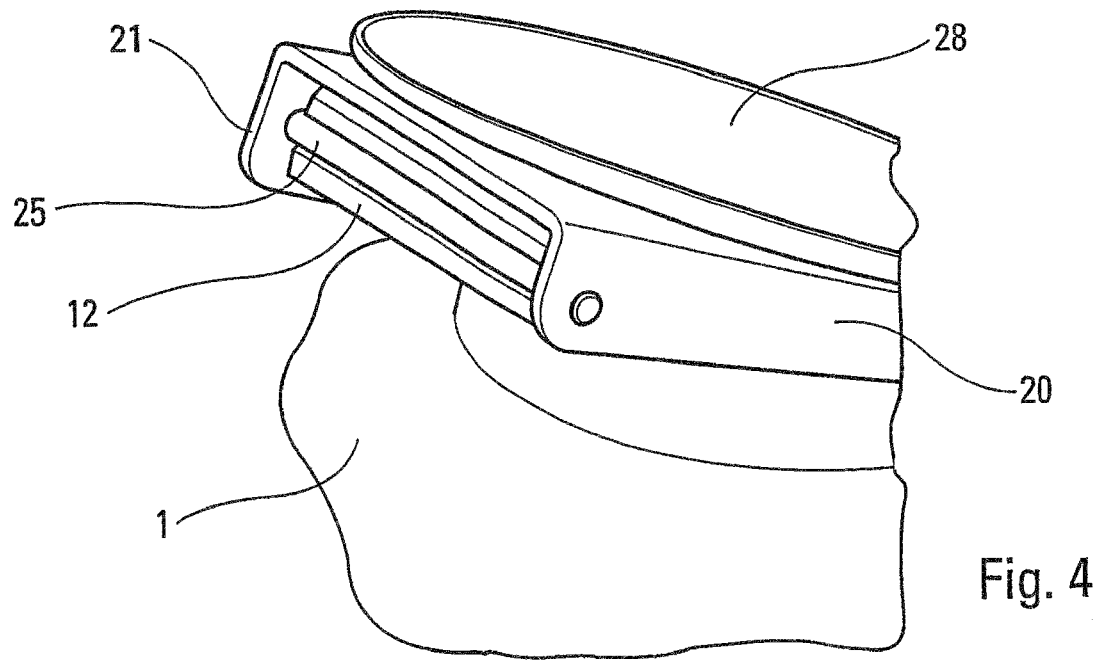
FIG. 4 is a partial perspective view corresponding to the arrow IV in FIG. 2D.

As is illustrated schematically in FIGS. 2A, 2B, 2C and 2D, the body 1 can be fitted particularly easily and precisely on the bezel 3 after the pin 19 has been placed in the conduit 18:
- first, the bezel 2 is brought up close to the bezel 3 such that the transverse groove 16 is facing, and close to, the transverse shaft 25 (the transverse groove and transverse shaft also known as a "hooking unit") (see FIG. 2A);
- the bezels 2 and 3 are brought closer together until the rear ends of the longitudinal faces 10, 11 and 20, 21 cooperate with one another to serve as guide means (see FIG. 2B);
- then the transverse shaft 25 is fastened in the transverse groove 16, this fastening being possible only if the bezels 2 and 3 are centered with respect to each other, this being achieved by cooperation of said rear ends of the longitudinal faces 20 and 21 of the bezel 3 and the rear ends of the longitudinal faces 10 and 11 of the bezel 2. The bezels 2 and 3 are then situated in the relative position illustrated by FIGS. 2C and 3;
- finally, as is indicated by the arrow F in FIG. 2C, the bezel 2 is folded onto the bezel 3 in such a way that the hook or hooks 26 extend into the notch or notches 17 and lock elastically on the pin 19. During this folding, the bezels 2 and 3 are guided relative to each other by the cooperation of the longitudinal faces 10, 11, 20 and 21. This therefore is the operative position shown schematically in FIG. 2D and illustrated by FIGS. 4, 5 and 6. It will be noted that the front face 22, located between the elastic hooks 26, is rigid and prevents snap-fitting of the bezels 2 and 3 if the shaft 25 is not correctly engaged in the groove 16. This guarantees correct axial positioning of the bezels and avoids high stresses on the hooks 26.

Starting from this operative position, it is easy, if so required, to disconnect the bezels 2 and 3 by taking the pin 19 out of the conduit 18. The anchoring of the hook or hooks 26 on the bezel 2 is canceled such that the body 1 can be tilted about the shaft 25, then separated from the bezel 3.

In order to facilitate the maneuvering of the pin 19, its grip end 19a is designed in such a way as to avoid any rotation when it is taken hold of by surgical forceps. For this purpose, it comprises at least two diametrically opposite flats 19b. Moreover, in order to ensure that said pin does not leave its seat 18 during the maneuvering of the bezel 2, its grip end is traversed by an orifice 19c through which a tie 30 is passed in order to attach said pin 19 to the bezel 2 (see FIG. 3).

The invention claimed is:

1. A heart prosthesis implantable in the pericardial cavity of a patient, said prosthesis being able to replace the natural left and right ventricles of said patient after the removal of said natural left and right ventricles, the heart prosthesis comprising a rigid body in which artificial left and right ventricles are arranged, said artificial ventricles being provided with a connection unit for connection to the natural left and right auricles of said patient, the connection unit comprising:
   a first bezel forming an integral part of said rigid body and comprising first and second orifices, which communicate respectively with the artificial left ventricle and with the artificial right ventricle; and
   a second bezel comprising third and fourth orifices that can be connected respectively to said natural left auricle and to said natural right auricle,
   said first and second bezels being able to be connected to each other removably, in order to assume an operative position in which said first and third orifices are located opposite each other and said second and fourth orifices are located opposite each other,
   wherein the connection unit further comprises:
   a hooking unit for hooking one end of one of the bezels to the other bezel, said hooking unit being able to permit folding of said bezels relative to each other;
   a guide unit for guiding said bezels relative to each other before and during said hooking and also during said folding; and
   a snap-fit unit for engaging said bezels on each other in said operative position corresponding to the end of said folding.

2. The heart prosthesis according to claim 1, wherein said snap-fit unit is situated, relative to said bezels, remote from said hooking unit.

3. The heart prosthesis according to claim 1, wherein said snap-fit unit comprises one or more elastic hooks carried by one of said bezels, and an anchoring unit, for anchoring said elastic hooks, carried by the other of said bezels, said anchoring unit being removable from the bezel that carries said anchoring unit.

4. The heart prosthesis according to claim 3, wherein said removable anchoring unit is formed by a pin that can slide transversely in said bezel that carries said anchoring unit.

5. The heart prosthesis according to claim 4, wherein a grip end of the pin comprises a grip unit allowing said grip end to be taken hold of securely by surgical forceps.

6. The heart prosthesis according to claim 4, wherein an attachment unit is provided for attaching said pin to the bezel carrying said pin during the maneuvers for connection of said bezels.

7. The heart prosthesis according to claim 1, wherein said hooking unit comprises a transverse shaft carried by one of said bezels, and a transverse groove which is formed in the other of said bezels and in which said transverse shaft can lodge itself.

8. The heart prosthesis according to claim 1, wherein said guide unit comprises at least one longitudinal face on said first bezel and at least one longitudinal face on said second bezel, said longitudinal faces of said first and second bezels coming into contact with one another before said hooking, and sliding on one another during said hooking and said folding.

9. The heart prosthesis according to claim 1, wherein said first and second bezels each have the general shape of a right-angled parallelepiped, said second bezel being able to serve as a cover fitted laterally on said first bezel.

* * * * *